United States Patent [19]

Lawson et al.

[11] Patent Number: 5,059,204
[45] Date of Patent: Oct. 22, 1991

[54] OCULAR CUTTER WITH ENHANCED CUTTING ACTION

[75] Inventors: William C. Lawson, Willow Grove; Jude V. Paganelli, New Britain; Perry Sepielli, Richboro, all of Pa.

[73] Assignee: Site Microsurgical Systems, Inc., Horsham, Pa.

[21] Appl. No.: 427,284

[22] Filed: Oct. 26, 1989

[51] Int. Cl.$^5$ ............................................. A61B 17/32
[52] U.S. Cl. .................................................... 606/171
[58] Field of Search ................ 606/170, 171; 604/22; 30/241, 278, 220

[56] References Cited

U.S. PATENT DOCUMENTS

| 3,815,604 | 6/1974 | O'Malley et al. | 606/171 X |
|---|---|---|---|
| 3,884,238 | 5/1975 | O'Malley et al. | 128/305 |
| 4,099,529 | 7/1978 | Peyman | 606/171 |
| 4,200,106 | 4/1980 | Douvas et al. | 128/305 |
| 4,210,146 | 7/1980 | Banko | 606/171 |
| 4,428,748 | 1/1984 | Peyman et al. | 604/22 |
| 4,508,532 | 4/1985 | Drews et al. | 604/22 |
| 4,517,977 | 5/1985 | Frost | 606/170 |
| 4,530,356 | 7/1985 | Helfgott et al. | 606/171 |
| 4,573,576 | 4/1986 | Krol | 206/471 |
| 4,603,694 | 8/1986 | Wheeler | 606/171 |
| 4,611,400 | 9/1986 | Drake | 30/353 |
| 4,642,090 | 2/1987 | Utrata | 604/22 |
| 4,662,869 | 5/1987 | Wright | 604/22 |
| 4,674,502 | 6/1987 | Imonti | 128/305 |
| 4,696,298 | 9/1987 | Higgins | 128/305 |
| 4,753,234 | 6/1988 | Martinez | 606/171 |
| 4,790,312 | 12/1988 | Capuano, Sr. et al. | 128/305 |
| 4,819,635 | 4/1989 | Shapiro | 128/305 |

Primary Examiner—Michael H. Thaler
Attorney, Agent, or Firm—Paul A. Coletti

[57] ABSTRACT

The inner needle in a guillotine type ocular cutter is ground and placed within the swaged outer needle in an interference fit, so that a radial force is exerted by said inner needle on said outer needle to better shear the ocular tissue. Further, a positive stop is effected on the drive shaft controlling the inner needle so that the distance from the end of the outer needle port to the tissue is minimized. Alternately, the drive shaft has a dwell exerted on it.

8 Claims, 3 Drawing Sheets

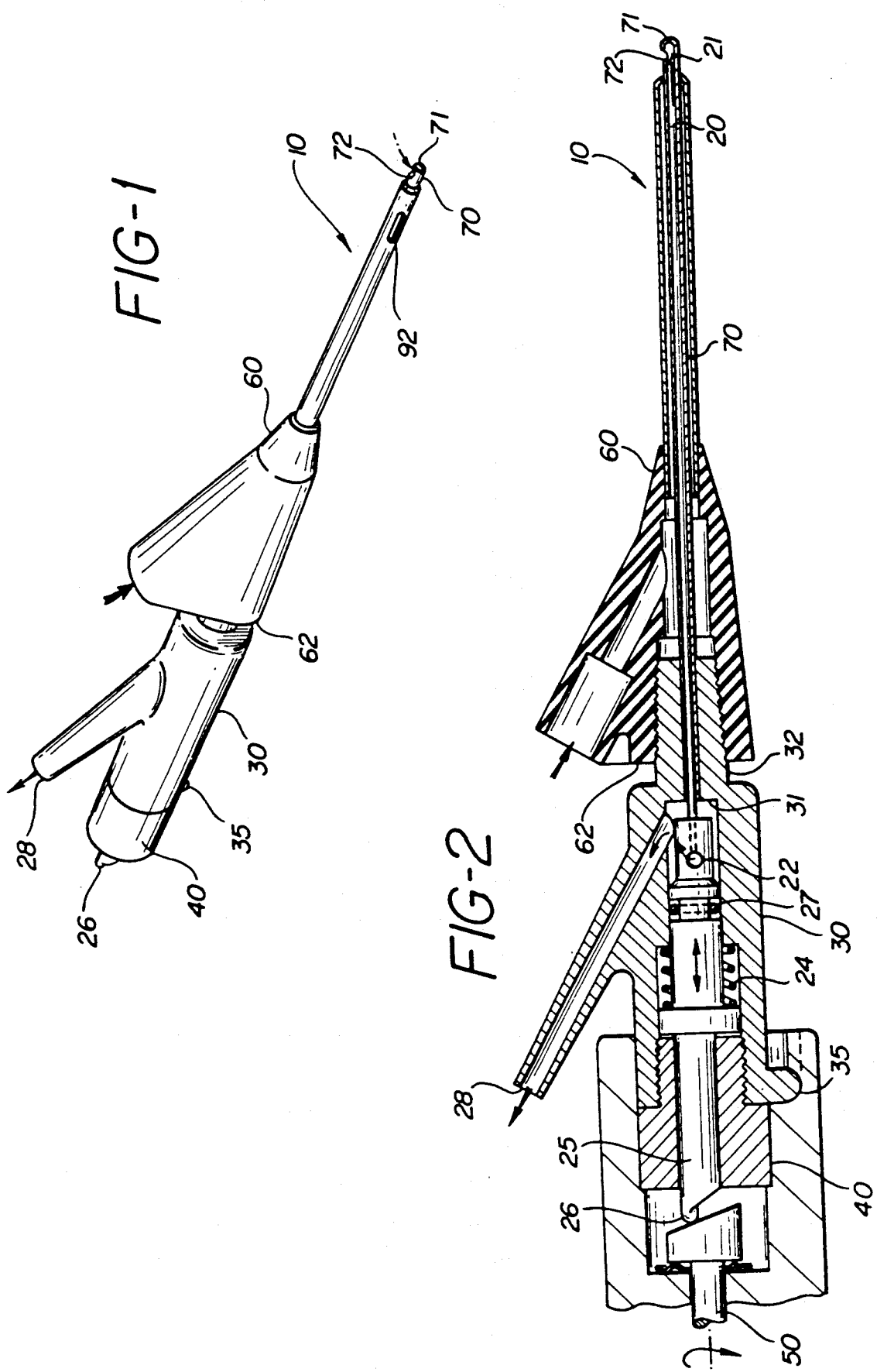

OCULAR CUTTER WITH ENHANCED CUTTING ACTION

FIELD OF THE INVENTION

The invention relates generally to the field of tissue removal. More specifically, the invention relates to ocular cutters for tissue removal. Most specifically, the invention relates to ocular cutters for tissue removal where the ocular cutter has enhanced cutting action.

BACKGROUND OF THE INVENTION

In recent years, tissue removal devices have become quite commonplace. Generally, in the field of ocular surgery, tissue removal devices have been found in the form of phacoemulsification devices, as well as ocular cutters. In an ocular cutter, there has generally been found a double needle configuration where an outer chamber or "needle" is concentric with an inner "needle". In the outer needle there is an open port, and the inner needle reciprocates within that open port. Tissue is sucked into the port of the outer needle by vacuum pressure within the inner chamber. When the inner needle reciprocates past the open port, the tissue is sheared. The tissue is then removed down the length of the inner needle by suction.

While these "guillotine" type ocular cutters have been successful instruments, they have posed certain drawbacks. First, there has always been an incentive to provide for the most precise cutting mechanism. The more precise the cutter is, the less chance of tissue trauma. The risk of improper amounts of tissue, or cutting the improper size of the tissue, is also reduced. Frequently, however there is incomplete shear of tissue at the outer needle port.

Second, because the port of the outer needle generally is designed at a distance from the end of the outer needle, present ocular cutters all have a certain minimum width of tissue from the point of contact with the ocular cutter which can not be cut. When cutting takes place, there is always this tolerance which must be taken into account before cutting. Thus, the cutting approach may not be applicable for small, precise cuts which require cutting at the point of contact with healthy ocular tissue.

SUMMARY OF THE INVENTION

Accordingly, it is an object of the invention to provide an ocular cutter having an outer needle and an inner needle with an enhanced cutting surface on the inner needle. It is further an object of the invention to provide an ocular cutter where the inner needle is formed so that controlled, desired amounts of tissue are cut.

It is yet another object of the invention to provide an ocular cutter having an inner needle reciprocable within an outer needle such that the inner needle produces a precise cut between the outer needle and the tissue.

It is another object of the invention to provide an ocular cutter having an inner needle reciprocable within an outer needle such that the distance between the location of cutting and the contact point between outer needle and tissue is minimized.

It is finally an object of the invention to provide an ocular cutter having an inner needle reciprocable within an outer needle such that the location of cutting is moved closer to the point of contact between inner and outer needle of the cutter.

These and other objects of the invention are accomplished in an ocular cutter having an inner needle reciprocable within an outer needle. Within the outer needle there is a port into which tissue is pulled by a suction mechanism provided along the length of the inner needle. The outer needle is swaged to a controlled inner diameter. The outer diameter of the inner needle is oversized for the swaged inner diameter of the outer needle. Thus, the inner needle is placed within the outer needle in an interference fit at the swaged area, but maintains clearance over the remaining length of insertion within the outer needle. Therefore, when the inner needle reciprocates within the outer needle, there is a radial force, like a spring, on the inner needle at its point of contact with the outer needle. This causes a larger and more accurate shear force on the tissue to be cut. Therefore, the tissue is more readily cut, with minimized adverse effects, such as tissue trauma.

When the inner needle reciprocates within the outer needle, the outer needle port is placed a minimum distance from the end of the outer needle. In order to minimize the distance between the location of the port and the end of the outer needle, the inner needle is reciprocated such that there is a positive stop made on the reciprocation of the inner needle. The inner needle is free to travel nearly the entire length of the outer needle. Thus, the inner needle makes a sharp cut across the entire outer needle port. Again, the tissue is more precisely cut. Because the outer needle port is positioned close to the end of the outer needle, the distance between the point of contact of the tissue and the port is reduced. Also, improvements are made to the drive mechanism of the cutter to respond to slightly misoriented parts or any eccentricities in the drive shaft. This maximizes the usefulness of cutting possible at the outer needle port, and makes the presently improved ocular cutter more efficient for a varied number of uses.

These and other aspects of the invention will be better understood from the following figures and the detailed description which follow.

DETAILED DESCRIPTION OF THE DRAWINGS

The accompanying drawings will better describe the invention:

FIG. 1 is a perspective view of an ocular cutter of the invention;

FIG. 2 is an assembly drawing in cross-section of an ocular cutter of the invention;

DETAILED DESCRIPTION OF THE INVENTION

Figure 3:
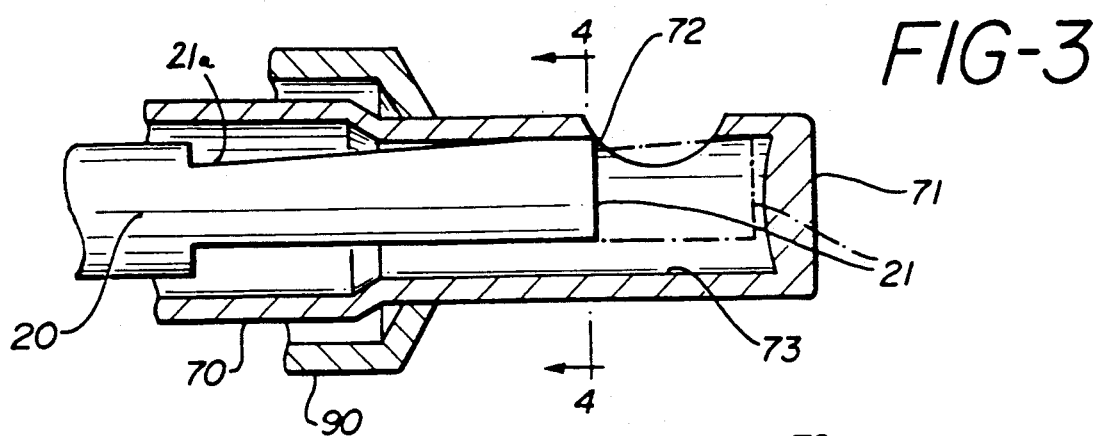
FIG. 3 is an enlarged detail view of the ocular cutter of the invention at the tip with the inner needle placed within the outer needle.

As can be seen in FIGS. 1 and 2, the ocular cutter 10 of the present invention has inner needle 20 attached to a reciprocable shaft 25. The inner needle 20 is generally hollow and shaft 25 contains an outlet 22 for aspiration. Aspiration line 28 ensures suction of the displaced tissue away from the cutting site at the end of the needle. Shaft 25 reciprocates within the aspiration sleeve 30, and includes eccentric end 26. This end 26 interacts with spring loaded cam or wobble plate 50, which rotates. Upon rotation, the reciprocable shaft 25 is moved longitudinally, due to the force from the cam or wobble plate 50 onto the eccentric end 26 of the shaft. The inner needle 20 and reciprocable shaft 25 are generally forced away from the cutting site by means of the spring 24. Spring 24 overcomes the forces at the cutting site as well as the force of the O-ring seal 27, which seals shaft 25 to the cutter housing or aspiration sleeve 30.

Aspiration takes place at aspiration line 28 and through the hollow inner needle 20 via aspiration outlet 22 on reciprocable shaft 25. Aspiration sleeve 30 fits on handpiece 40 by means of the bayonet pin 35, as seen in FIG. 2. In addition, flexible elastomer infusion sleeve 60 fits over the collar 32 of the aspiration sleeve 30. The cylindrical body 62 of infusion sleeve 60 seals around collar 32 of aspiration sleeve 30 in an interference fit. This allows the surgeon to adjust the relationship between infusion tip 90 and port 72, within about one-sixteenth inch. The infusion sleeve 60 provides the proper fluid flow within infusion tip 90 over the outer needle 70.

At the end of the infusion sleeve 60 is infusion tip 90 which fits over outer needle 70. The outer needle 70 fits over the inner needle 20 so that the inner needle 20 is reciprocable within the outer needle 70. Outer needle 70 contains port 72, through which the tissue is aspirated. Tissue is pulled into port 72 by the vacuum created by an aspiration mechanism through hollow inner needle 20. When the inner needle 20 reciprocates in the outer needle 70 by means of the wobble plate 50 and the reciprocating shaft 25, the end of the inner needle 20 shears the ocular tissue exposed within outer needle 70 through outer needle port 72. The tissue has been infused with fluid from the infusion sleeve 60 through infusion tip 90 and infusion port 92. Once the tissue is sheared, it is aspirated out of the instrument via the aspiration sleeve 28.

Figure 4:
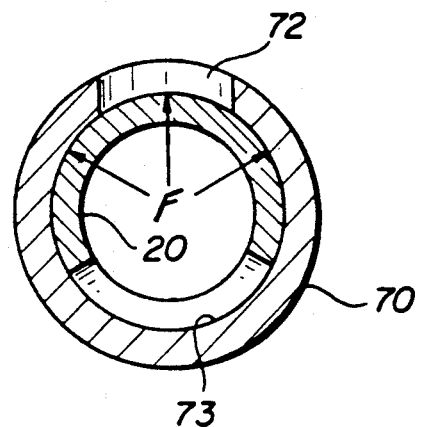
FIG. 4 is a cross-sectional view of the inner needle within the outer needle at lines 4—4 of FIG. 3.

As can be further seen from FIGS. 3 and 4, the outer needle 70 is swaged at its end 71 slightly reducing the diameter of outer needle 70. Swaging creates a more uniform inner diameter 73 and improves the surface finish of outer needle inner diameter 73. This creates a better interference fit with inner needle 20, and improves cutting. Inner diameter 73 is also slightly tapered toward its end, so that inner needle 20 may be received within outer needle 70. Strategically, inner needle 20 is sized so that its outer diameter is larger than the inner diameter 73 of outer needle 70 at the swaged end 71. There is clearance between inner needle 20 and outer needle 70 over the remaining length of outer needle 70, back toward the aspiration sleeve 30.

When inner needle 20 is inserted into the outer needle 70 and reciprocates within the outer needle 70, inner needle end 21 reciprocates within outer needle swaged end 71. Inner needle 20 is ground at end 21 so that the circumference of inner needle 20 has an arc of about one quarter the circumference removed at end 21. A tapered relief 21a is also provided on the external surface of inner needle end 21 to create clearance within outer needle 70 all around inner needle 20, except for the end 21 of inner needle 20.

When inner needle 21 reciprocates, there is an outward radial force from the inner needle end 21 on the outer needle inner diameter 73, based on the deflection of the inner needle end 21 in order to create the interference fit within the outer needle inner diameter 73. The outer radial force F causes the inner needle 20 to press more firmly against the inner diameter 73 of the outer needle 70. The tapered relief 21a of outer needle end 21 is sufficiently large to create contact at only inner needle end 21 reciprocating within swaged outer needle end 71. The pliability of tapered relief 21a insures deflection of end 21.

The enhanced inner needle 20, in combination with the outer needle 70, acts as a shear mechanism, like a scissors. Because the inner needle end 21 experiences an outward force, it remains forced against the outer needle 70, even though tissue to be cut is lodged in the inner needle path as the inner needle 20 reciprocates. Therefore, the ocular tissue is sheared at its point of contact with the outer needle port 72. It has been found that the force between needles 20, 70 is greater and more uniform, because of the improved fit between needles 20, 70. The shear that takes place at the outer needle port 72 is more stark and precise, resulting in a more accurate cutting motion created by the inner needle 20.

Figure 5:
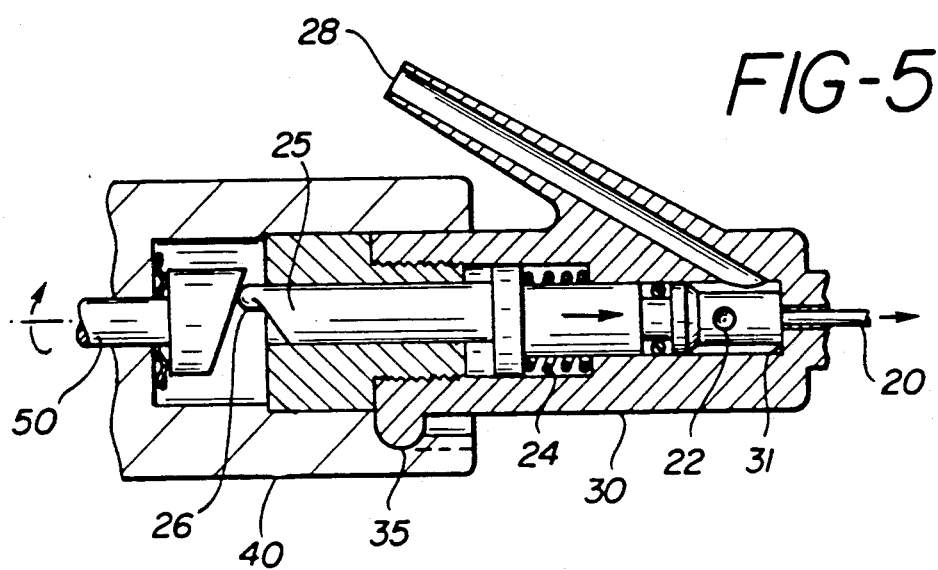
FIG. 5 is a view of the positive stop mechanism in the reciprocable shaft within the aspiration housing.
Figure 6:
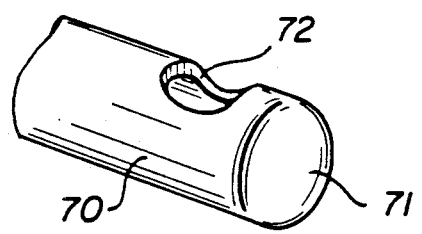
FIG. 6 is a perspective view of an end of the outer needle.

Also, it is to be noticed in FIGS. 5 and 6 that reciprocating shaft 25 is sized to be longer than the distance from the motorized cam 50 at its maximum stroke to the inner end 31 of aspiration sleeve 30. Therefore, as the cam 50 begins to rotate, the shaft 25 meets a positive stop at the end 31 of aspiration sleeve 30. This positive stop is put to use at the end of the two needles 20, 70. The inner needle 20 is configured so that the distance between the inner needle end 21 and the outer needle end 71 is minimized. The outer needle port 72 is placed as close as can be manufactured to the outer needle end 71. Because it is now easy to manufacture inner needle 20 to reach the inside of outer needle end 71, it is certain that the inner needle 20 will cut all the tissue which remains in the outer needle port 72 when the inner needle 20 reciprocates across outer needle port 72. Because the outer needle port 72 is placed close to the end 71 of the outer needle 70, the actual site for cutting ocular tissue is made very close to the outer needle end 71. Thus, greater accuracy is obtained in the positioning of the outer needle 70 at the tissue which is to be cut. Tolerances for the margin between the outer needle end 71 and the tissue contacting the outer needle end 71 are reduced. The present ocular cutter therefore operates with more utility and can perform a wider variety of procedures.

Figure 7:
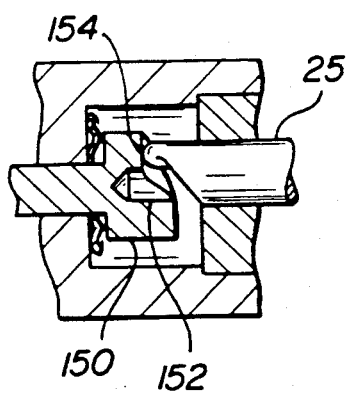
FIG. 7 is a cross-sectional view of an alternate embodiment of the cam used in the invention.
Figure 8:
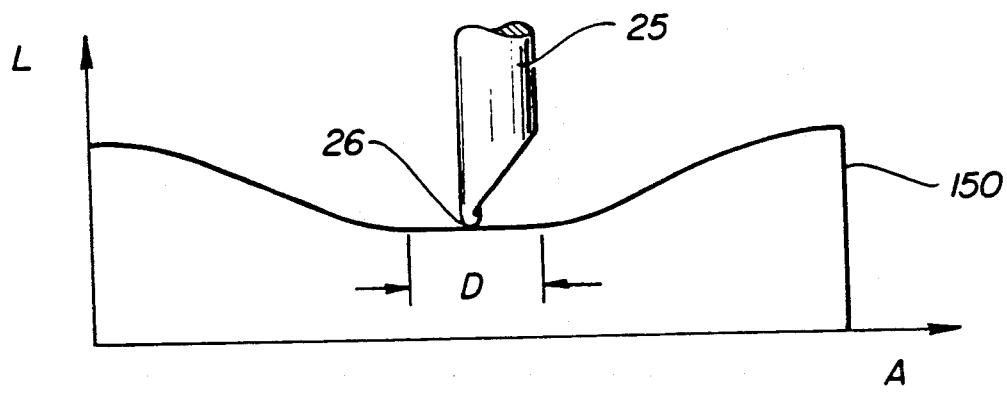
FIG. 8 is a graph of the motion of the cam in FIG. 7.

Alternately, as seen in FIG. 7, cam 150 may be used in place of cam 50. This cam has a longitudinal displacement L, as seen in FIG. 8. Essentially cam 150 is machined so that there is an approximately 15° to 30° dwell D. Also, cam 150 has a central bore 152, around which is machined positional edge 154, for interaction with eccentric end 26 of shaft 25. Positional edge 154, in profile, is machined so that at any angular position A along cam 150, positional edge 154 will displace eccentric end 26 longitudinally by the same amount regardless of radial location of eccentric end 26. Thus, tolerances on the position of eccentric end are negated by uniformity of positional edge 154. Also, the dwell D seen in FIG. 8 functions such that when cam 150 is oriented at no stroke, cam 150 accommodates variations in angular position A of eccentric end 26 up to 30° without any longitudinal displacement.

It is to be understood that the invention has been disclosed in relation to a particularly preferred embodiment, but that the invention is to be derived from the appended claims and their equivalents.

What is claimed is:

1. A tissue cutter comprising:

a hollow inner needle with an elongated end and circular cross-section; and an outer needle with circular cross-section enclosing an open inner portion, said outer needle closed at one end, and said outer needle circular cross-section containing an opening near said one end for the insertion of tissue; said inner needle reciprocable within the inner portion of said outer needle; and a rotary can means wherein said inner needle reciprocates by motion against said cam means having a dwell at the end of the stroke of said inner needle within said outer needle, said dwell extending at least 15 degrees of angular rotation of said rotary cam means;

wherein the outer circumference of said inner needle is generally smaller than the inner circumference of said outer needle; and wherein the outer circumference of said elongated end gradually increases distally along said inner needle length;

such that at said elongated end, the outer circumference of said inner needle: (a) fits within the inner circumference of said outer needle in an interference fit; and (b) has an arc greater than 120° along it circular cross-section removed.

2. The tissue cutter of claim 1 wherein said inner needle reciprocates with a positive stop at the end of said inner needle reciprocation within said outer needle.

3. The tissue cutter of claim 2 wherein said positive stop is effectuated at a drive shaft attached to said inner needle such that said drive shaft abuts said outer needle at the end of said inner needle reciprocation, thereby preventing said inner needle from further entering said outer needle.

4. The tissue cutter of claim 1 wherein said outer needle end is swaged.

5. The tissue cutter of claim 4 wherein said removed arc forms a partial cylinder along the elongated end of said inner needle.

6. The cutter of claim 5 wherein said outer needle is taper toward said outer needle end to enhance the interference fit with said inner needle.

7. The cutter of claim 5 wherein said drive shaft abuts the end of said outer needle in a positive stop at the end of the stroke of said inner needle.

8. The cutter of claim 1 wherein said outer needle is tapered toward said outer needle end to enhance the interference fit with said inner needle.

* * * * *

UNITED STATES PATENT AND TRADEMARK OFFICE
CERTIFICATE OF CORRECTION

PATENT NO. : 5,059,204
DATED : October 22, 1991
INVENTOR(S) : William C. Lawson; Jude V. Paganelli; and Perry Sepielli It is certified that error appears in the above-identified patent and that said Letters Patent is hereby corrected as shown below:

Claim 1, Column 6, Line 3 "it" should be -- its --.

Signed and Sealed this

Eighteenth Day of January, 1994

Attest:

BRUCE LEHMAN

Attesting Officer

Commissioner of Patents and Trademarks